(12) United States Patent
Teirstein et al.

(10) Patent No.: US 6,485,489 B2
(45) Date of Patent: Nov. 26, 2002

(54) CATHETER SYSTEM FOR REPAIRING A MITRAL VALVE ANNULUS

(75) Inventors: Paul Teirstein, La Jolla, CA (US); John A. Osth, Laguna Hills, CA (US); Thomas H. Witzel, Laguna Nigel, CA (US); Cary Hata, Tustin, CA (US); Wallace N Hauck, Irvine, CA (US); Hosheng Tu, Newport Coast, CA (US)

(73) Assignee: Quantum Cor, Inc., Irvine, CA (US)

( * ) Notice: Subject to any disclaimer, the term of this patent is extended or adjusted under 35 U.S.C. 154(b) by 0 days.

(21) Appl. No.: 10/101,230

(22) Filed: Mar. 19, 2002

(65) Prior Publication Data

US 2002/0115994 A1 Aug. 22, 2002

Related U.S. Application Data

(63) Continuation-in-part of application No. 10/083,264, filed on Oct. 22, 2001, which is a continuation-in-part of application No. 09/410,902, filed on Oct. 2, 1999, now Pat. No. 6,306,133.

(51) Int. Cl.[7] ............................................. A61B 18/18
(52) U.S. Cl. ............................. 606/41; 606/46; 606/47; 607/102
(58) Field of Search ............................... 606/41–52, 27, 606/32; 607/96, 97, 101, 122

(56) References Cited

U.S. PATENT DOCUMENTS

| | | | |
|---|---|---|---|
| 3,656,185 A | | 4/1972 | Carpentier |
| 4,164,046 A | | 8/1979 | Cooley |
| 5,100,429 A | | 3/1992 | Sinofsky |
| 5,443,496 A | * | 8/1995 | Shturman ..................... 606/41 |
| 5,456,662 A | | 10/1995 | Edwards et al. |
| 5,546,954 A | | 8/1996 | Yamada |
| 5,669,934 A | | 9/1997 | Sawyer |
| 5,674,279 A | | 10/1997 | Wright et al. |
| 5,823,956 A | * | 10/1998 | Roth et al. ..................... 606/41 |
| 5,947,977 A | | 9/1999 | Slepian et al. |
| 6,083,219 A | * | 7/2000 | Laufer ......................... 606/27 |
| 6,258,087 B1 | | 7/2001 | Edwards et al. |
| 6,267,781 B1 | | 7/2001 | Tu |
| 6,283,962 B1 | | 9/2001 | Tu et al. |
| 6,284,284 B1 | | 9/2001 | Naughton |
| 6,303,765 B1 | | 10/2001 | Bandman et al. |
| 6,306,133 B1 | | 10/2001 | Tu et al. |

\* cited by examiner

*Primary Examiner*—Linda C. M. Dvorak
*Assistant Examiner*—David M. Ruddy

(57) ABSTRACT

A catheter system and methods for repairing a valvular annulus or an annular organ structure of a patient comprising sandwiching and compressing the annulus and applying heat sufficient to shrink or tighten tissue surrounding the annulus defect.

18 Claims, 15 Drawing Sheets

CATHETER SYSTEM FOR REPAIRING A MITRAL VALVE ANNULUS

CROSS REFERENCE TO RELATED APPLICATION

This application is a continuation-in-part of application Ser. No. 10/083,264, filed on Oct. 22, 2001, which is a continuation-in-part of application Ser. No. 09/410,902 filed Oct. 2, 1999, now U.S. Pat. No. 6,306,133, all of which are incorporated by reference herein in its entirety.

FIELD OF THE INVENTION

The present invention generally relates to a system and methods for applying therapeutic energy to a patient for medical purposes such as reducing and/or shrinking a tissue mass. More particularly, the invention relates to an ablation catheter system that selectively contacts the tissue of a valvular annulus in order to tighten and stabilize an annular organ structure adapted for repairing an annular organ structure defect of a patient.

BACKGROUND OF THE INVENTION

The circulatory system consists of a heart and blood vessels. In its path through the heart, the blood encounters four valves. The valve on the right side that separates the right atrium from the right ventricle has three cusps and is called the tricuspid valve. It closes when the ventricle contracts during a phase known as systole and it opens when the ventricle relaxes, a phase known as diastole.

The pulmonary valve separates the right ventricle from the pulmonary artery. It opens during systole, to allow the blood to be pumped toward the lungs, and it closes during diastole to keep the blood from leaking back into the heart from the pulmonary artery. The pulmonary valve has three cusps, each one resembling a crescent and it is also known as a semi-lunar valve.

The mitral valve, so named because of its resemblance to a bishop's mitre, is in the left ventricle and it separates the left atrium from the ventricle. It opens during diastole to allow the blood stored in the atrium to pour into the ventricle, and it closes during systole to prevent blood from leaking back into the atrium. The mitral valve and the tricuspid valve differ significantly in anatomy. The annulus of the mitral valve is somewhat D-shaped whereas the annulus of the tricuspid valve is more nearly circular.

The fourth valve is the aortic valve. It separates the left ventricle from the aorta. It has three semi-lunar cusps and it closely resembles the pulmonary valve. The aortic valve opens during systole allowing a stream of blood to enter the aorta and it closes during diastole to prevent any of the blood from leaking back into the left ventricle.

In a venous circulatory system, a venous valve is to prevent the venous blood from leaking back into the upstream side so that the venous blood can return to the heart and the lungs for blood oxygenating purposes.

Clinical experience has shown that repair of a valve, either a heart valve or a venous valve, produces better long-term results than does valve replacement. Valve replacement using a tissue valve suffers long-term calcification problems. On the other hand, anticoagulation medicine, such as heparin, is required for the life of a patient when a mechanical valve is used in valve replacement. The current technology for valve repair or valve replacement requires an expensive open-heart surgery that needs a prolonged period of recovery. A less invasive catheter-based valve repair technology becomes an unmet clinical challenge.

The effects of valvular dysfunction vary. Mitral regurgitation has more severe physiological consequences to the patient than does tricuspid valve regurgitation. In patients with valvular insufficiency it is an increasingly common surgical practice to retail the natural valve, and to attempt to correct the defects. Many of the defects are associated with dilation of the valve annulus. This dilatation not only prevents competence of the valve but also results in distortion of the normal shape of the valve orifice or valve leaflets. Remodeling of the annulus is therefore central to most reconstructive procedures for the mitral valve.

As a part of the valve repair it is either necessary to diminish or constrict the involved segment of the annulus so that the leaflets may coapt correctly on closing, or to stabilize the annulus to prevent post-operative dilatation from occurring. The current open-heart approach is by implantation of a prosthetic ring, such as a Cosgrove Ring or a Carpentier Ring, in the supra annular position. The purpose of the ring is to restrict and/or support the annulus to correct and/or prevent valvular insufficiency. In tricuspid valve repair, constriction of the annulus usually takes place in the posterior leaflet segment and in a small portion of the adjacent anterior leaflet.

Various prostheses have been described for use in conjunction with mitral or tricuspid valve repair. The ring developed by Dr. Alain Carpentier (U.S. Pat. No. 3,656,185) is rigid and flat. An open ring valve prosthesis as described in U.S. Pat. No. 4,164,046 comprises a uniquely shaped open ring valve prosthesis having a special velour exterior for effecting mitral and tricuspid annuloplasty. The fully flexible annuloplasty ring could only be shortened in the posterior segment by the placement of placating sutures. John Wright et al. in U.S. Pat. No. 5,674,279 discloses a suturing ring suitable for use on heart valve prosthetic devices for securing such devices in the heart or other annular tissue. All of the above valve repair or replacement requires an open-heart operation which is costly and exposes a patient to higher risk and longer recovery than a catheter-based less invasive procedure.

Moderate heat is known to tighten and shrink the collagen tissue as illustrated in U.S. Pat. No. 5,456,662 and U. S. Pat. No. 5,546,954. It is also clinically verified that thermal energy is capable of denaturing the tissue and modulating the collagenous molecules in such a way that treated tissue becomes more resilient ("The Next Wave in Minimally Invasive Surgery" MD&DI pp. 36–44, August 1998). Therefore, it becomes imperative to treat the inner walls of an annular organ structure of a heart valve, a valve leaflet, chordae tendinae, papillary muscles, and the like by shrinking/tightening techniques. The same shrinking/tightening techniques are also applicable to stabilize injected biomaterial to repair the defect annular organ structure, wherein the injectable biomaterial is suitable for penetration and heat-initiated shrinking/tightening.

One method of reducing the size of tissues in situ has been used in the treatment of many diseases, or as an adjunct to surgical removal procedures. This method applies appropriate heat to the tissues, and causes them to shrink and tighten. It can be performed on a minimal invasive fashion, which is often less traumatic than surgical procedures and may be the only alternative method, wherein other procedures are unsafe or ineffective. Ablative treatment devices have an advantage because of the use of a therapeutic energy that is rapidly dissipated and reduced to a non-destructive level by conduction and convection, to other natural processes.

Radiofrequency (RF) therapeutic protocol has been proven to be highly effective when used by electrophysiologists for the treatment of tachycardia, atrial flutter and atrial fibrillation; by neurosurgeons for the treatment of Parkinson's disease; by otolaryngologist for clearing airway obstruction and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the device-to-tissue contact site to obtain the desired temperature for treating a tissue or for effecting the desired shrinking of the host collagen or injected biomaterial adapted to immobilize the biomaterial in place.

Edwards et al. in U.S. Pat. No. 6,258,087, entire contents of which are incorporated herein by reference, discloses an expandable electrode assembly comprising a support basket formed from an array of spines for forming lesions to treat dysfunction in sphincters. Electrodes carried by the spines are intended to penetrate the tissue region upon expansion of the basket. However, the assembly disclosed by Edwards et al. does not teach a tissue-contactor member comprising a narrow middle region between an enlarged distal region and an enlarged proximal region suitable for sandwiching and compressing the sphincter for tissue treatment.

Tu in U.S. Pat. No. 6,267,781 teaches an ablation device for treating valvular annulus or valvular organ structure of a patient, comprising a flexible elongate tubular shaft having a deployable spiral wire electrode at its distal end adapted to contact/penetrate the tissue to be treated and to apply high frequency energy to the tissue for therapeutic purposes. Tu et al. in U.S. Pat. No. 6,283,962 discloses a medical ablation device system for treating valvular annulus wherein an elongate tubular element comprises an electrode disposed at its distal section that is extendible from an opening at one side of the tubular element, the energy generator, and means for generating rotational sweeping force at the distal section of the tubular element to effect the heat treatment and the rotational sweeping massage therapy for target tissues. Both patents, entire contents of which are incorporated herein by reference, teach only the local tissue shrinkage, not for treating simultaneously a substantial portion of the valvular annulus.

Therefore, there is a clinical need to have a less invasive catheter-based approach for repairing an annular organ structure of a heart valve, a valve leaflet, chordae tendinae, papillary muscles, and the tissue defect by using high frequency energy for reducing and/or shrinking a tissue mass, with optionally an injected biomaterial along with the host tissue mass for tightening and stabilizing the dilated tissue adjacent a valvular annulus.

SUMMARY OF THE INVENTION

In general, it is an object of the present invention to provide a catheter system and methods for repairing an annular organ structure of a heart valve, an annular organ structure of a venous valve, a valve leaflet, chordae tendinae, papillary muscles, a sphincter, and the like.

It is another object of the present invention to provide a catheter system and methods by using high frequency current for tissue treatment or repairing and causing the tissue to shrink or tighten.

It is still another object to provide a catheter-based less invasive system that contacts the tissue of an annulus in order to tighten and stabilize a substantial portion of the dysfunctional annular organ structure simultaneously or sequentially.

It is a preferred object to provide a method for repairing a valvular annulus defect comprising injecting a heat shapeable biomaterial formulated for in vivo administration by injection via a delivery system at a site of the valvular annulus defect; and applying heat sufficient to shape the biomaterial and immobilize the biomaterial at about the annulus defect.

It is another preferred object of the present invention to provide a flexible tissue-contactor member located at the distal tip section of a catheter shaft for compressively sandwiching and contacting an inner wall of an annular organ structure, wherein the tissue-contactor member includes an expandable structure having a narrow middle region and enlarged end regions that is generally configured to snugly fit and sandwich the inner wall of an annular organ structure for optimal therapy that is characterized by exerting compression onto the inner wall.

It is another object of the invention to provide a method for repairing a tissue defect comprising: injecting a heat shapeable biomaterial formulated for in vivo administration by injection via a percutaneous delivery system at a site of the tissue defect; and applying heat to the biomaterial and a portion of the tissue defect adapted for shaping the biomaterial, the heat being below a temperature sufficient for effecting crosslinking of the biomaterial and the portion of the tissue defect.

It is still another object of the present invention to provide a catheter system and methods for providing high frequency current energy to the tissue needed for treatment at or adjacent an annular organ structure.

In one embodiment, the method for operating a catheter system for repairing a valvular annulus or a valveless annulus comprising compressively sandwiching the annulus by a tissue-contactor member and delivering high frequency energy to the annulus, wherein the tissue-contactor member is configured to have a narrow middle region between an enlarged distal region and an enlarged proximal region adapted for compressively sandwiching the annulus at about the middle region for subsequent tissue treatment.

The catheter system of the present invention has several significant advantages over known catheters or ablation techniques for repairing an annular organ structure of a heart valve, a valve leaflet, chordae tendinae, papillary muscles, venous valve, and the like. In particular, the ablation catheter of this invention by using high frequency current energy for reducing and/or shrinking a tissue mass may tighten and stabilize the dilated tissue at or adjacent a valvular annulus.

BRIEF DESCRIPTION OF THE DRAWING

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

The following descriptions of the preferred embodiment of the invention are exemplary, rather than limiting, and many variations and modifications are within the scope of the invention. What is shown in FIGS. 1 to 15 is an embodiment of the present invention to provide a catheter system that selectively contacts the tissue of an annulus in order to tighten and stabilize an annular organ structure adapted for repairing an annular organ structure defect of a patient.

"Sandwich" as a verb is herein meant to make into between usually two things of another quality or character; particularly intended to mean confining an annulus between two radially enlarged end regions of a tissue-contactor member characterized by certain degrees of compression onto the annulus exerted from the two end regions.

It is one object of the present invention to provide a method for repairing a valvular annulus defect comprising injecting a heat shapeable biomaterial formulated for in vivo administration by injection via a delivery system at a site of the valvular annulus defect; and applying heat sufficient to shape the biomaterial and immobilize the biomaterial at about the annulus defect.

Figure 1:
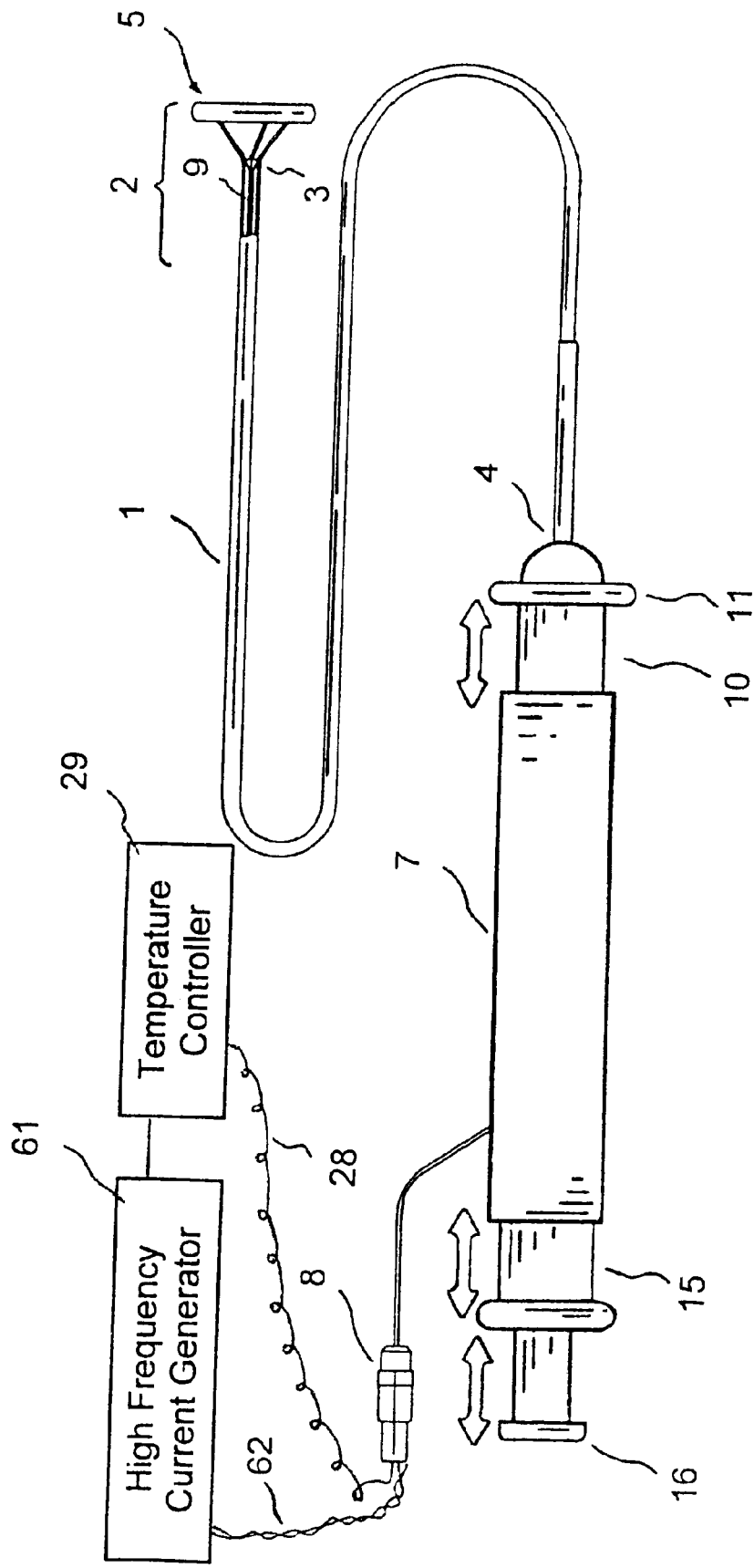
FIG. 1 is an overall view of a catheter system having a flexible tissue-contactor member and electrode element means at its distal tip section constructed in accordance with the principles of the present invention.

FIG. 1 shows an overall view of one embodiment of a catheter-based high-frequency treatment system having a flexible tissue-contactor member and an electrode element means at its distal tip section constructed in accordance with the principles of the present invention. A catheter system constructed in accordance with the principles of the present invention comprises a flexible catheter shaft 1 having a distal tip section 2, a distal end 3, a proximal end 4, and at least one lumen 14 extending therebetween.

In one embodiment, the catheter system comprises a flexible, relatively semi-rigid tissue-contactor member 5 located at the distal tip section 2 and inside the at least one lumen 14 of the catheter shaft 1 for contacting an inner wall 51 of an annular organ structure 52 when deployed. The tissue-contactor members may have certain variations (35 in FIG. 8 and 45 in FIG. 10) sharing the common characteristics of having a narrow middle region between a first radially enlarged proximal region and a second radially enlarged distal region suitable for compressively sandwiching the inner wall 51 of the annular organ structure 52 for effectively applying tissue-shrinkable energy site-specifically. It is believed that "compressively sandwiching the inner wall of the annular organ structure" is a significant requirement and one particular embodiment of the present invention for effectively applying tissue-shrinkable energy site-specifically.

The tissue-contactor member 5 is deployable out of the at least one lumen 14 by a tissue-contactor deployment mechanism 15 located at a handle 7. The tissue-contactor member 5 is preformed or expandable to have an appropriate shape configured to fit with the inner wall 51 of the annular organ structure 52. The tissue-contactor member 5 may be selected from the group consisting of a circular ring, a D-shaped ring, a kidney-shaped ring, an oval ring, and other round-shaped construct.

The handle 7 is attached to the proximal end 4 of the catheter shaft 1. The handle comprises the tissue-contactor deployment mechanism 15 and an electrode deployment means 16 for advancing the electrode element means 9 out of the tissue-contactor member 5. The electrode element means intended for shrinking tissue of an annular organ structure may comprise needle electrodes 9 in FIG. 6, or other variations such as the one made of conductive elastomer material on a balloon (37, 38, 39 in FIG. 9) or a basket electrode element 48 in FIG. 13.

A connector 8 secured at the proximal end of the catheter system, is part of the handle section 7. The handle has one optional steering mechanism 10. The steering mechanism 10 is to deflect the distal tip section 2 of the catheter shaft 1 for catheter maneuvering and positioning. In one preferred embodiment, by pushing forward the front plunger 11 of the handle 7, the distal tip section 2 of the catheter shaft deflects to one direction. By pulling back the front plunger 11, the tip section returns to its neutral position. In another embodiment, the steering mechanism 10 at the handle 7 comprises means for providing a plurality of deflectable curves on the distal tip section 2 of the catheter shaft 1.

The catheter system also comprises a high frequency current generator 61, wherein an electrical conductor means 62 for transmitting high frequency current to the electrode element means (9 in FIG. 1, 35 in FIG. 8 or 45 in FIG. 10) is provided. One object of the present invention is to provide high frequency heat to collagen of tissue to a temperature range of about 45° C. to 75° C. or higher for at least a few seconds to cause collagen to shrink a fraction of its original dimension. The energy required from the high frequency current generator is generally less than 100 watts, preferably less than 10 watts.

The high frequency current may be selected from a group consisting of radiofrequency current, microwave current, ultrasound current, and combination thereof. Tu in U.S. Pat. No. 6,235,024, entire contents of which are incorporated herein by reference, discloses a catheter system having dual ablation capability of ultrasound current and radiofrequency current. The electrode element of the present invention may comprise a radiofrequency electrode, an ultrasound electrode (that is, transducer) or a combination thereof.

In one embodiment, the method may comprise percutaneously introducing the catheter system through a blood vessel to a site of the valvular annulus or introducing the catheter system through a thoroscopy port into a heart or injecting the heat shapeable biomaterial during an open-heart surgery. For other applications such as the sphincter treatment, the catheter may be introduced through a natural opening of the body. The application for sphincter treatment of the present invention comprises esophageal sphincter, urinary sphincter or the like. Small, ring-like muscles, called sphincters, surround portions of the alimentary canal. In a healthy person, these muscles contract or tighten in a coordinated fashion during eating and the ensuing digestive process, to temporarily close off one region of the alimentary canal from another.

For example, a muscular ring called the lower esophageal sphincter surrounds the opening between the esophagus and the stomach. The lower esophageal sphincter is a ring of increased thickness in the circular, smooth-muscle layer of the esophagus. Normally, the lower esophageal sphincter maintains a high-pressure zone between fifteen and thirty mm Hg above intragastric pressures inside the stomach. The catheter system and methods of the present invention may suitably apply to repair a sphincter annulus, other than the esophageal sphincter, in a patient.

Figure 2:
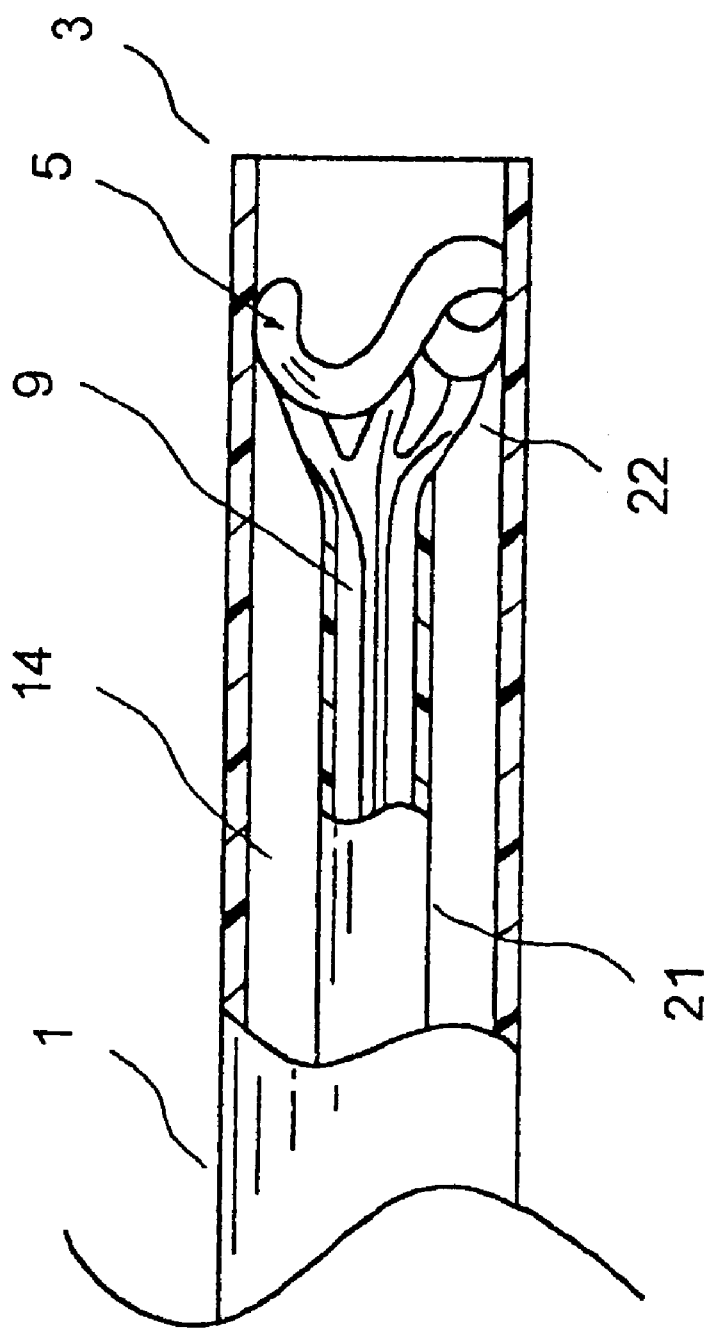
FIG. 2 is a close-up view of the distal tip section of the catheter system comprising a retracted tissue-contactor members with a retracted electrode element means at a non-deployed state.

FIG. 2 shows a close-up view of the distal tip section 2 of the catheter system comprising a retracted tissue-contactor member 5 with a retracted electrode element means 9 at a non-deployed state. Both the tissue-contactor member and the electrode element means are retractable to stay within the at least one lumen 14. This non-deployed state is used for a catheter to enter into and to withdraw from the body of a patient. The tissue-contactor member is generally preformed or constricted and flexible enough so that it can easily be retracted into the catheter lumen 14.

The tissue-contactor member 5 may be made of a biocompatible material selected from the group consisting of silicone, latex, polyurethane, fluoro-elastomer, polypropylene, polyethylene, polyethylene terephthalate, nylon, and a combination thereof. Reinforced substrate, such as mesh, wire, fiber, and the like, may be added to the tissue-contactor member 5 to make the tissue-contactor member semi-rigid so that when it is deployed, adequate pressure is exerted to the surrounding tissue for stabilizing its placement.

In one particular embodiment, the catheter system may comprise a needle electrode element means 9 located at or within the flexible tissue-contactor member 5 for penetrating into a tissue, such as an inner wall 51, wherein the needle electrode element means 9 is deployable out of the tissue-contactor member 5 in a manner essentially perpendicular to a longitudinal axis of the catheter shaft 1 when the needle electrode element means is deployed. In another preferred embodiment, the angle of the needle electrode against a tissue may be any suitable angle from 30 degrees to 150 degrees in reference to a longitudinal axis of the catheter shaft for effective tissue penetration.

The needle electrode element means 9 may comprise a plurality of needle electrodes 9A, 9B, 9C (shown in FIG. 6) that are preshaped to be essentially perpendicular to a longitudinal axis of the catheter shaft 1 when deployed. The high frequency current may be delivered to each of the plurality of needle electrodes 9A, 9B, 9C in a current delivery mode selected from the group consisting of individual delivery mode, pulsed delivery mode, sequential delivery mode, simultaneous delivery mode or a preprogrammed mode. The needle electrode element means 9 may be made of a material selected from the group consisting of platinum, iridium, gold, silver, stainless steel, tungsten, Nitinol, and other conducting material. The needle electrode element means 9 is connected to an electrode deployment means 16 at the handle 7 for advancing one or more needles of the needle electrode element means 9 out of the tissue-contactor member 5. This electrode deployment means may include various deployment modes selected from a group consisting of a single needle electrode deployment, a plurality of needle electrodes deployment or an all needle electrodes simultaneous deployment.

Figure 4:
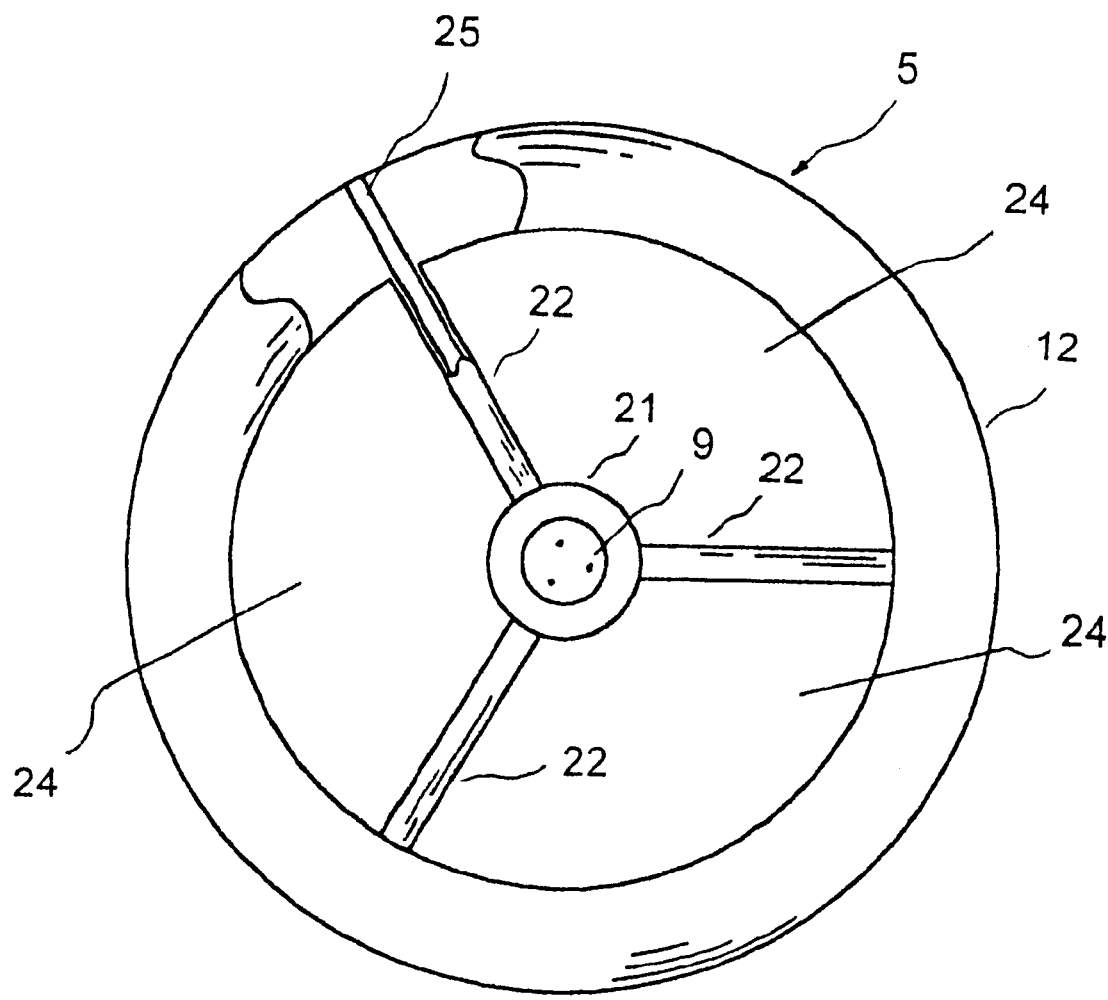
FIG. 4 is a front cross-sectional view, section I—I of FIG. 3, of the distal tip section of a catheter system comprising a deployed tissue-contactor member.

The "tissue-contactor member" in this invention is intended to mean a flexible semi-rigid element adapted for contacting an inner wall of an annular organ structure of a patient and is also preformed to have an appropriate shape compatible with the inner wall of the annular organ structure. The tissue-contactor member 5 may generally comprise a plurality of grooves or internal channels 25 (as shown in FIG. 4) so that a needle electrode of the needle electrode element means is able to deploy out of and retract into the tissue contactor means with minimal frictional resistance.

Figure 3:
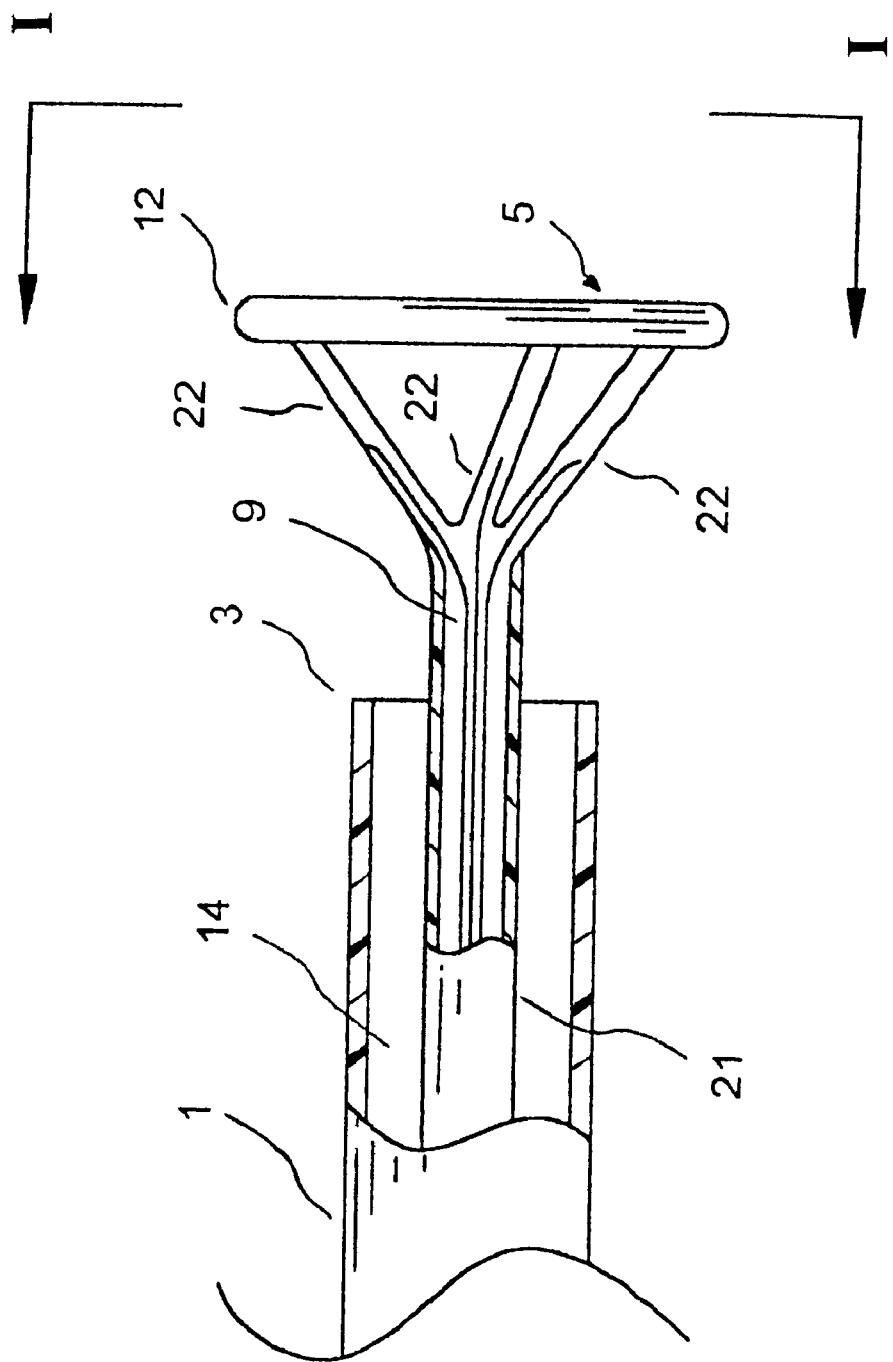
FIG. 3 is a close-up view of the distal tip section of the catheter system comprising a deployed tissue-contactor member having a retracted electrode element means.

FIG. 3 shows a close-up view of the distal tip section 2 of one embodiment of the catheter system comprising a deployed tissue-contactor member 5 and a retracted needle electrode element means 9. The outer diameter of the deployed tissue-contactor member 5 is optionally larger than the outer diameter of the catheter shaft 1 so that the outer rim 12 of the deployed tissue-contactor member may stably stay on the inner wall of the annular organ structure. A supporting member 21 along with a plurality of auxiliary supporting members 22 secured at the distal end of the supporting member 21 form a connecting means for connecting the tissue-contactor member 5 to the tissue-contactor deployment mechanism 15 that is located on the handle 7. The supporting member 21 and its auxiliary supporting members 22 are located within the at least one lumen 14 and have suitable torque transmittable property and adequate rigidity for deploying the tissue-contactor member 5.

The needle electrode of the first embodiment is preferably made of conductive material, while the surfaces of the catheter shaft 1, conducting wires 62, the supporting member 21 along with its auxiliary supporting members 22, are preferably covered/coated with an insulating material or electrically insulated.

In one preferred embodiment, the needle electrode is hollow with a fluid conduit connected to an external fluid source having a fluid injection mechanism. By "fluid" is meant an injectable shapeable biomaterial that is formulated for in vivo administration by injection via a delivery system at a site of the valvular annulus defect or tissue defect. By "tissue defect" is meant vulnerable plaque, calcified tissue, valvular annulus defect, annular defect, or other lesions of atherosclerosis.

FIG. 4 shows a front cross-sectional view; section I—I of FIG. 3, of the distal tip section of a catheter system comprising a deployed tissue-contactor member 5. The tissue-contactor member of the present invention in different improved embodiments adapted for serving the same indications of repairing tissue of an annular organ structure may comprise a plurality of open channels 24, pores and the like for a fluid or blood to pass from a proximal end of the tissue-contactor member to a distal end of the tissue-contactor member. The open channels may include macropores, micropores, openings, or combination thereof.

Figure 5:
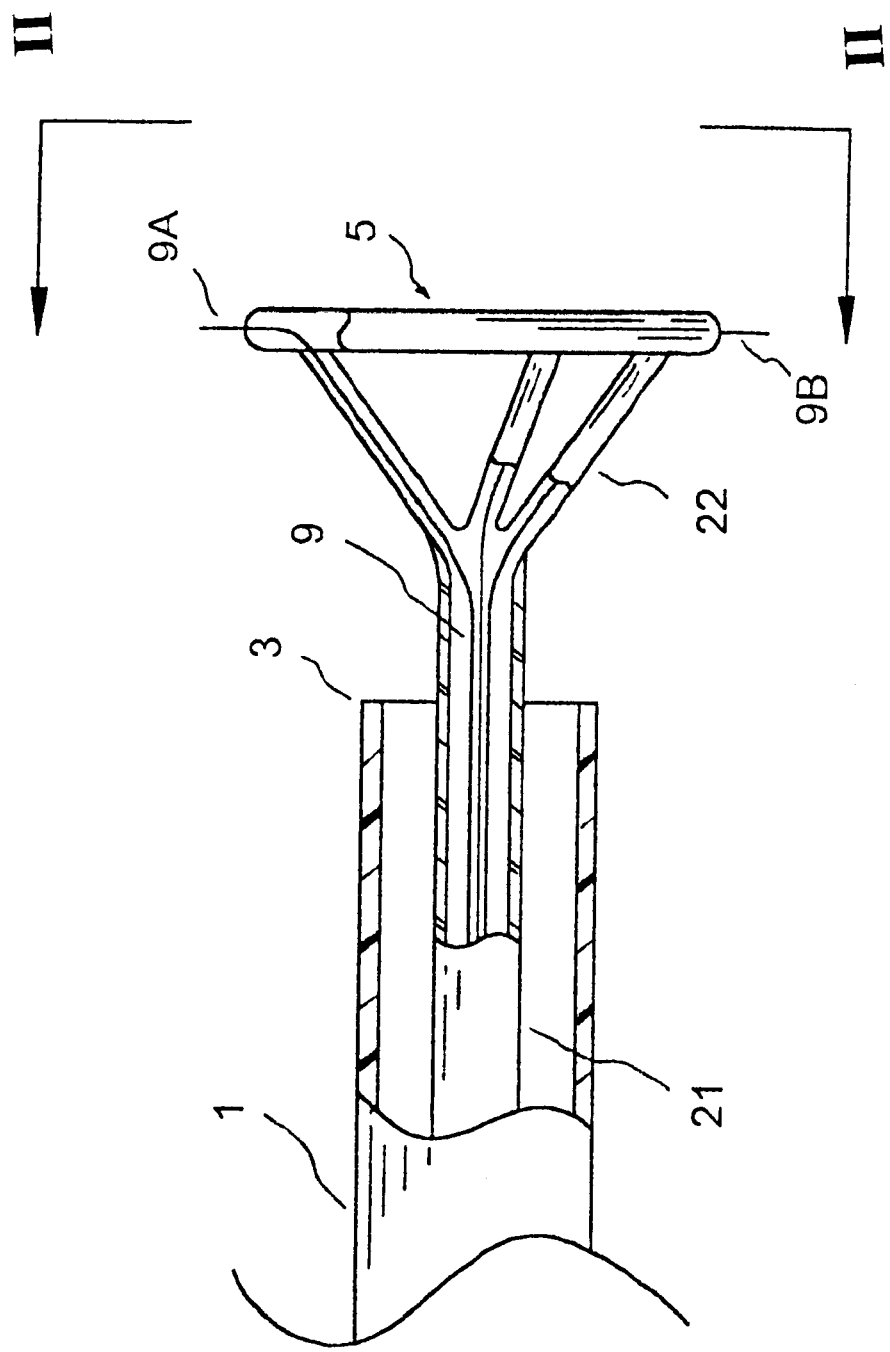
FIG. 5 is a close-up view of the distal tip section of the catheter system comprising a deployed tissue-contactor member and a deployed electrode element means at a fully deployed state.

FIG. 5 shows a close-up view of the distal tip section 2 of one embodiment of the current catheter system comprising a deployed tissue-contactor member 5 and a deployed needle electrode elements 9A, 9B at a fully deployed state. The fully deployed state is used for delivery of high frequency current energy to the needle electrode elements 9A, 9B and subsequently to the site-specific contact tissue for repairing the annular organ structure. The delivery of high frequency current to each of the needle electrode elements may go through a splitter or other mechanism. The needle electrode element means 9 is preformed so that when deployed, the needle electrodes are in a manner essentially perpendicular to a longitudinal axis of the catheter shaft 1 or at a suitable angle for effective thermal therapy.

Figure 6:
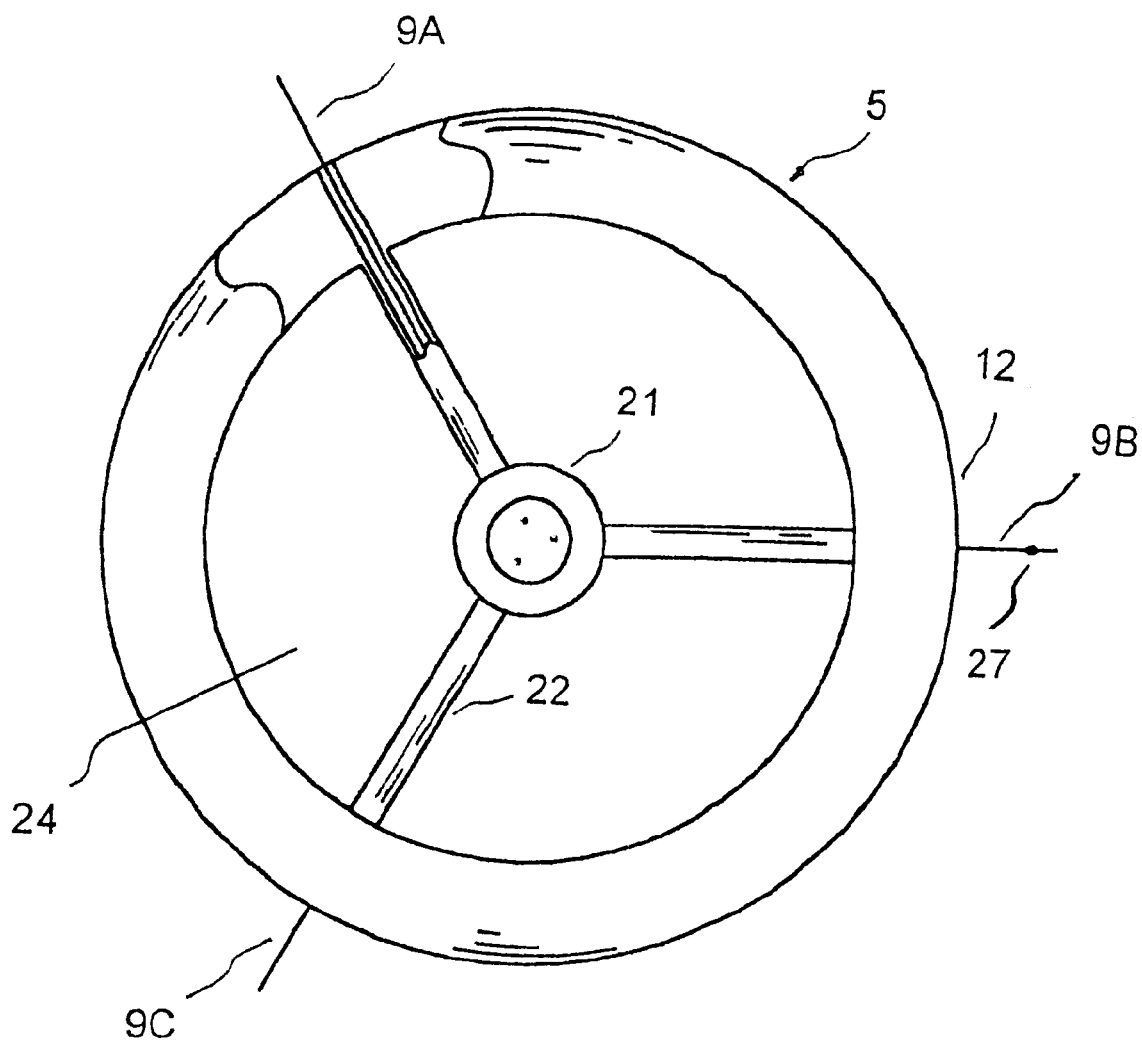
FIG. 6 is a front cross-sectional view, section II—II of FIG. 5, of the distal tip section of a catheter system comprising a deployed tissue-contactor member with a deployed electrode element means.

FIG. 6 shows a front cross-sectional view, section II—II of FIG. 5, of the distal tip section 2 of a catheter system comprising a deployed tissue-contactor member 5 and a deployed needle electrode element means 9. The tips of the needle electrodes 9A, 9B, and 9C extend out of the rim 12 of the tissue-contactor member 5 and penetrate into tissue for energy delivery.

Figure 7:
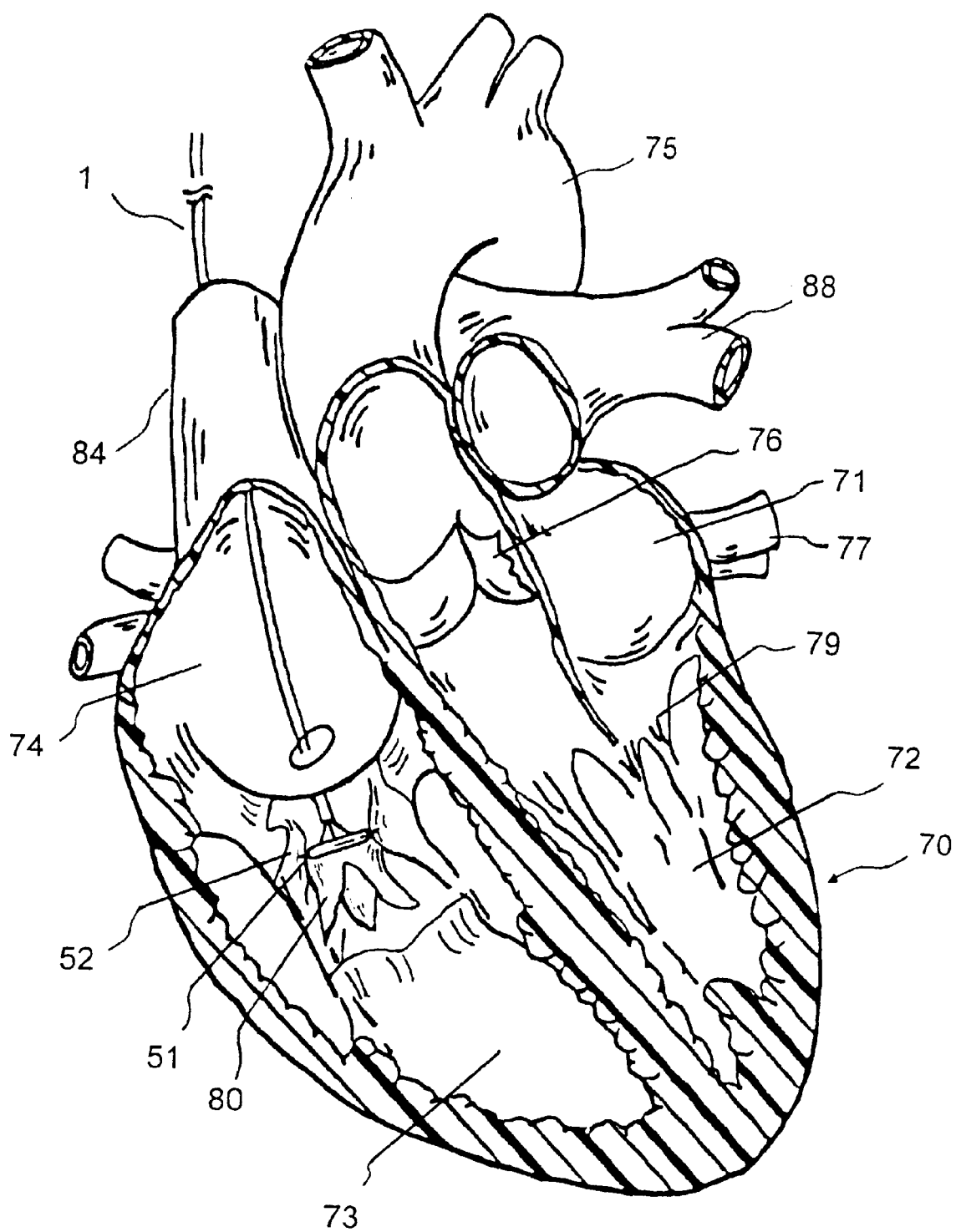
FIG. 7 is a simulated view of the catheter system of the present invention in contact with the tissue of an annular organ structure.

FIG. 7 shows a simulated view of the catheter system of the present invention in contact with the tissue 51 of an annular organ structure 52. The heart 70 has a left atrium 71, a left ventricle 72, a right ventricle 73, and a right atrium 74. Aorta 75 connects with the left ventricle 72 and contains an aorta valve 76. Pulmonary artery 77 connects with the right ventricle 73 through a pulmonary valve. Left atrium 71 communicates with the left ventricle 72 through a mitral valve 79. The right atrium 74 communicates with the right ventricle 73 through a tricuspid valve 80. Oxygenated blood is returned to the heat 70 via pulmonary veins 88. In a perspective illustration, a catheter is inserted into the right atrium 74 and is positioned on the inner wall 51 of the tricuspid valve 80. The leaflets of the tricuspid valve 80 open toward the ventricle side. Blood returned from the superior vena cava 84 and the opposite inferior vena cava flows into the right atrium 74. Subsequently, blood flows from the right atrium 74 to the right ventricle 73 through the tricuspid valve 80. Therefore, the tissue-contactor member 5 of the catheter shaft 1 does not interfere with the leaflet movement during the proposed less invasive thermal therapy of the invention.

Figure 8:
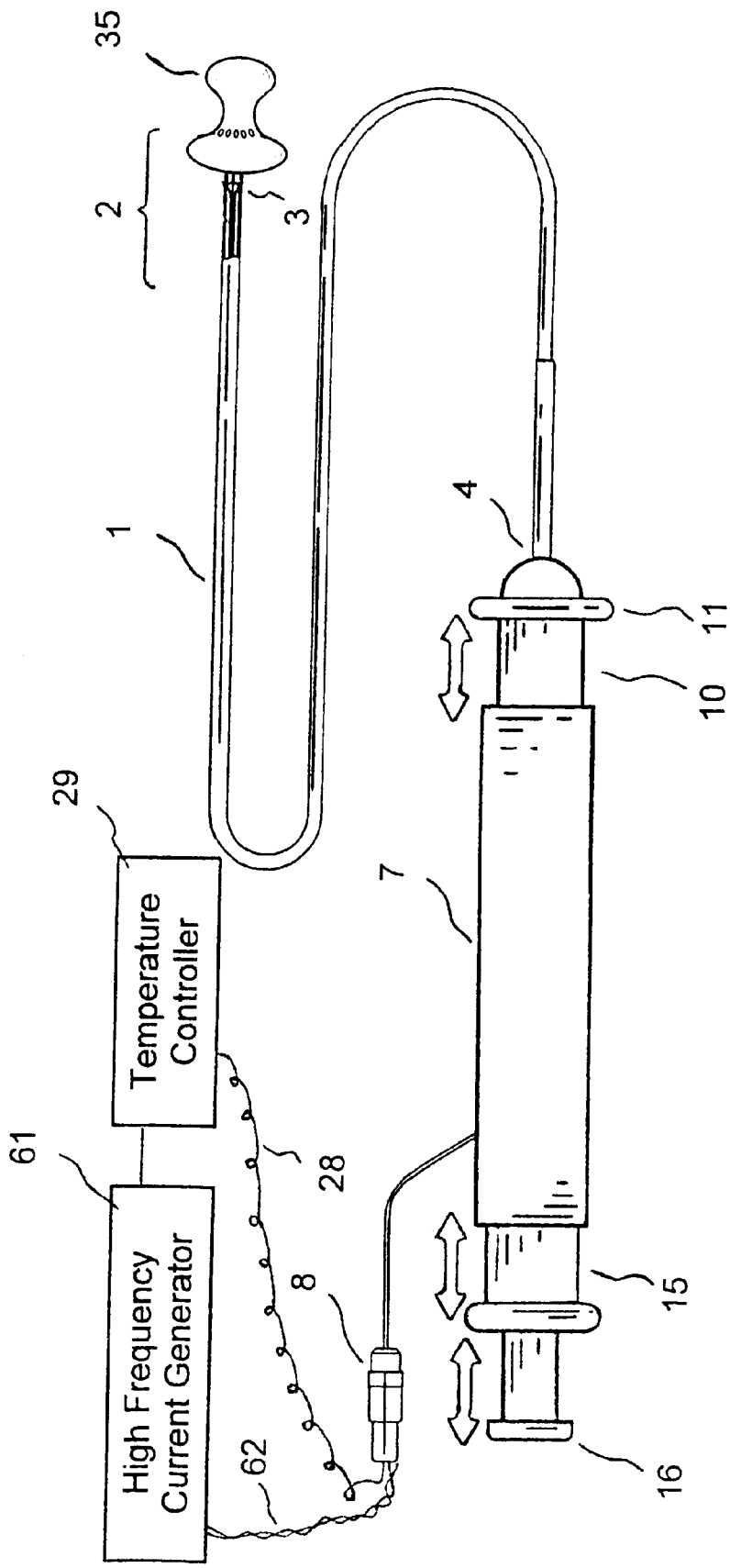
FIG. 8 is a first preferred embodiment of a catheter system having a deployed flexible tissue-contactor member and electrode element means at its distal tip section constructed in accordance with the principles of the present invention.

FIG. 8 shows a first preferred embodiment of a catheter system having a flexible tissue-contactor member 35 and electrode element means at its distal tip section 2 constructed in accordance with the principles of the present invention. As disclosed in the current invention, the tissue-contactor member 35 is retracted within one of the at least one lumen 14 during catheter insertion into and removal from the patient.

Figure 9:
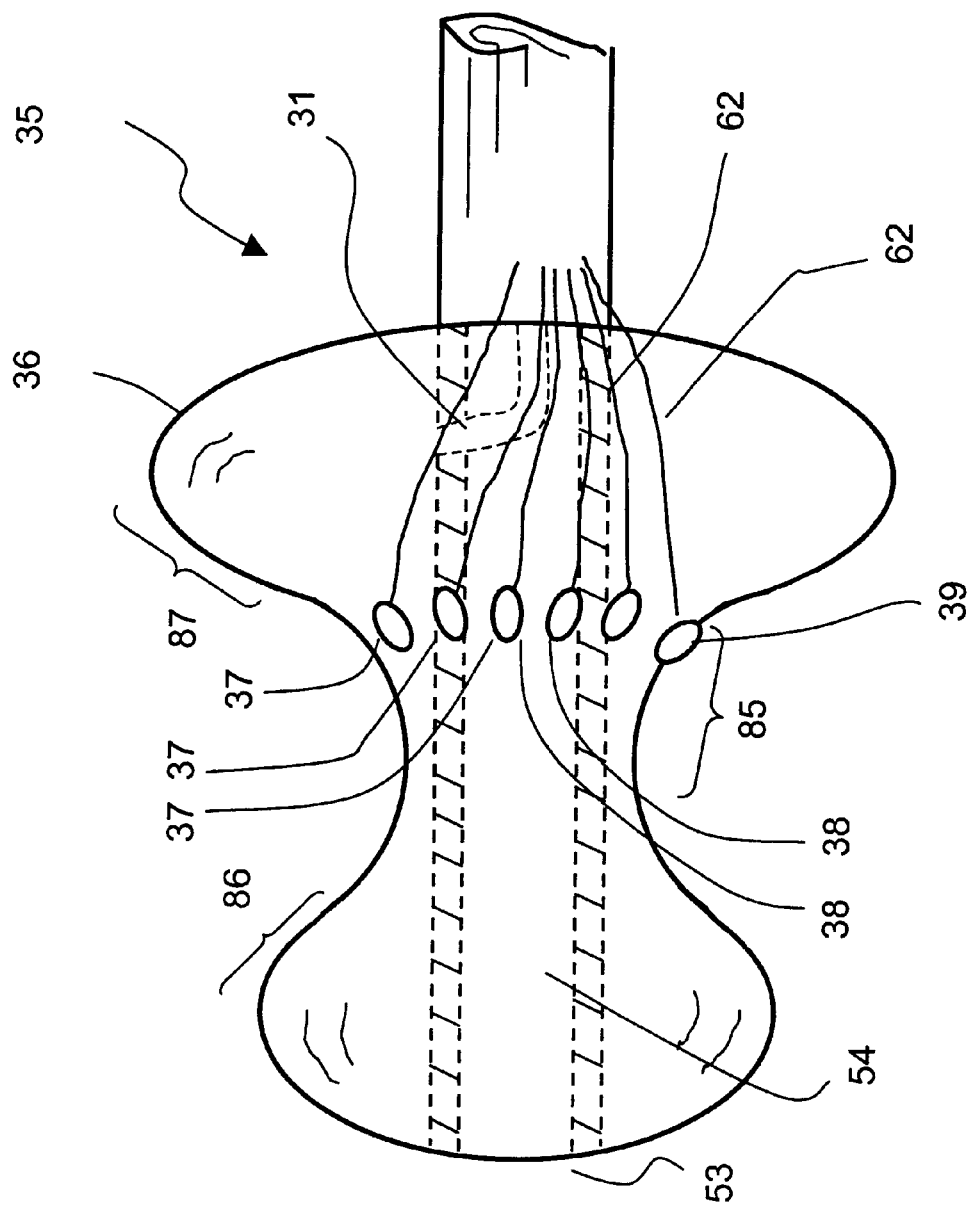
FIG. 9 is a detailed cross-sectional view of the distal tip section of the catheter system according to the first preferred embodiment in FIG. 8, comprising a deployed tissue-contactor member for treating the tissue of an annular organ structure.

FIG. 9 shows a detailed cross-sectional view of the distal tip section 2 of the catheter system according to FIG. 8, comprising a deployed tissue-contactor member 35 for treating the tissue of an annular organ structure. In a first preferred embodiment, the tissue-contactor member 35 may comprise a "double-mound" shaped balloon made of flexible expandable biocompatible material selected from a group consisting of silicone, latex, polyurethane, fluoro-elastomer, polypropylene, polyethylene, polyethylene terephthalate, nylon, and a combination thereof. The "double-mound" shape structure of the tissue-contactor member 35 or 45 is related generally to a structure that the tissue-contactor member is deployable out of the lumen of a catheter shaft and is expandable upon deployment configured to have a narrow middle region between an enlarged distal region and an enlarged proximal region (the so-called "double-mound" structure) suitable for compressively sandwiching the inner wall of the annular organ structure. The basic principle for the tissue-contactor member (such as 5 in FIG. 1, 35 in FIG. 8, 45 in FIG. 10, or 95 in FIG. 14) of the present invention is to compress the target tissue (annulus, sphincter, tumor and the like) for enhanced heat shrinkage/tightening on tissue. The compression may come from sandwich-type setup, such as from two opposite elements with the target tissue in between or from two elements at a suitable angle arrangement to compress the target tissue. In another embodiment, the "compressively sandwiching" a tissue is also herein intended to mean compression from two elements at a suitable angle arrangement to compress the target tissue as shown by two pairs of electrode elements (FIG. 15): the first electrode elements 96 compressing forwardly toward the distal end 53 and the second electrode elements 98 compressing radially toward the side of the target tissue.

In one illustrative example, the tissue-contactor member 35 in FIG. 9 as an expanded balloon comprises a radially enlarged proximal region 87, a middle region 85, and a radially enlarged distal region 86. The techniques to inflate and deflate a balloon 36 by infusing physiological liquid through a liquid passageway within the lumen 54 and the infusion opening 31 are well known to one who is skilled in the art and do not form a part of the present invention. The tissue-contactor member 35 may comprise a plurality of flexible electrode elements, wherein the electrode elements may be grouped 37, 38 or 39 for performing various modes of energy delivery selected from the group consisting of individual mode, pulsed mode, programmed mode, simultaneous mode, or combination thereof. The flexible electrode elements 37, 38, 39 may be made of conductive elastomer material or metal-containing conductive elastomer material selected from the group consisting of silicone, latex, polyurethane, fluoro-elastomer, nylon, and a combination thereof. The flexible electrode elements normally have similar expansion coefficient as that of the base balloon material and are securely bonded to the surface of the balloon 36 at appropriate locations so that each electrode becomes an integral part of the general tissue-contractor member 35. In the first embodiment, the balloon 36 may have an essentially hyperbolic shape with a neck region adapted for positioning the neck region at about the inner wall of the annular organ structure, wherein the plurality of electrode elements (37, 38 or 39 in FIG. 9) are positioned at about the neck region.

Figure 10:
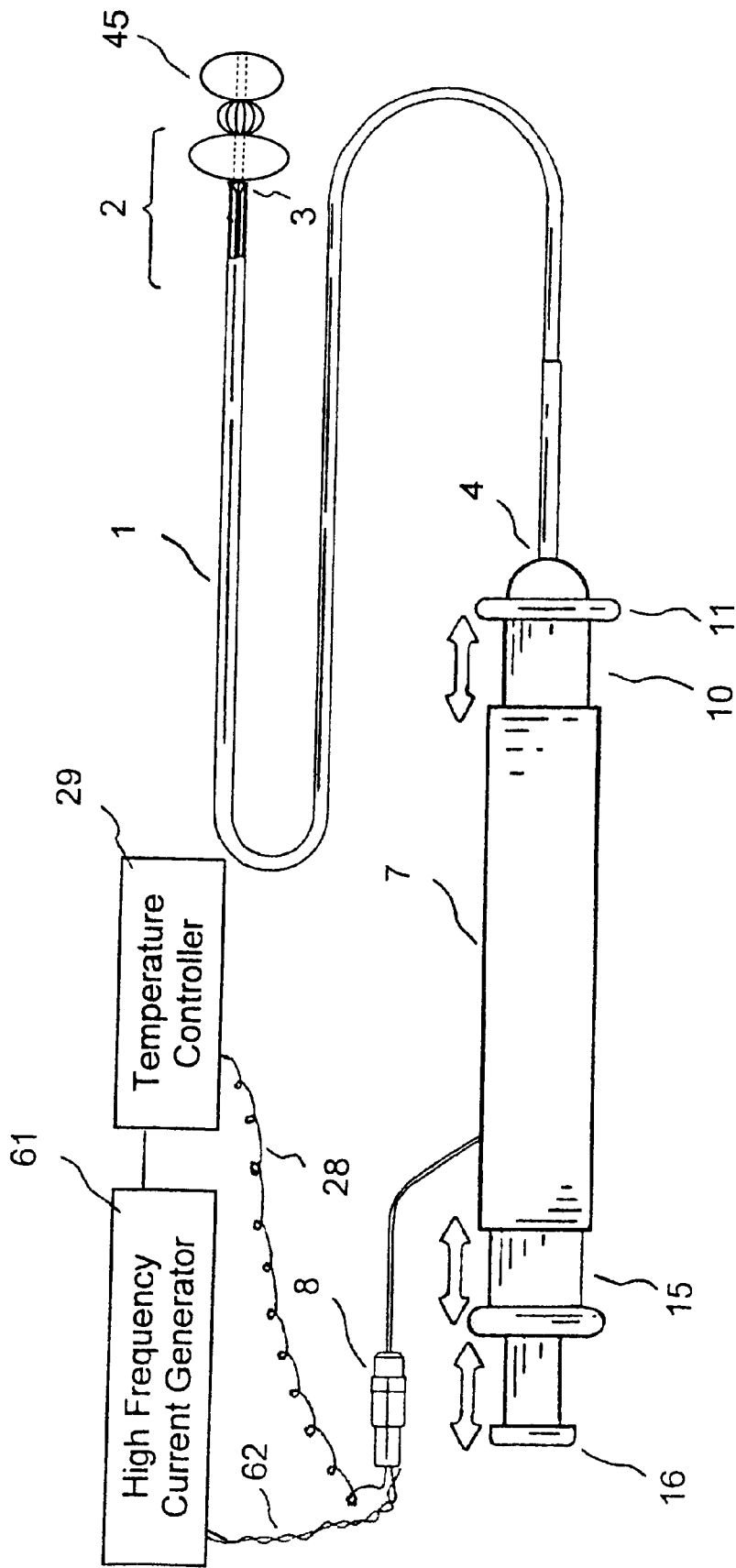
FIG. 10 is a second preferred embodiment of a catheter system having a deployed flexible tissue-contactor member and electrode element means at its distal tip section constructed in accordance with the principles of the present invention.
Figure 11:
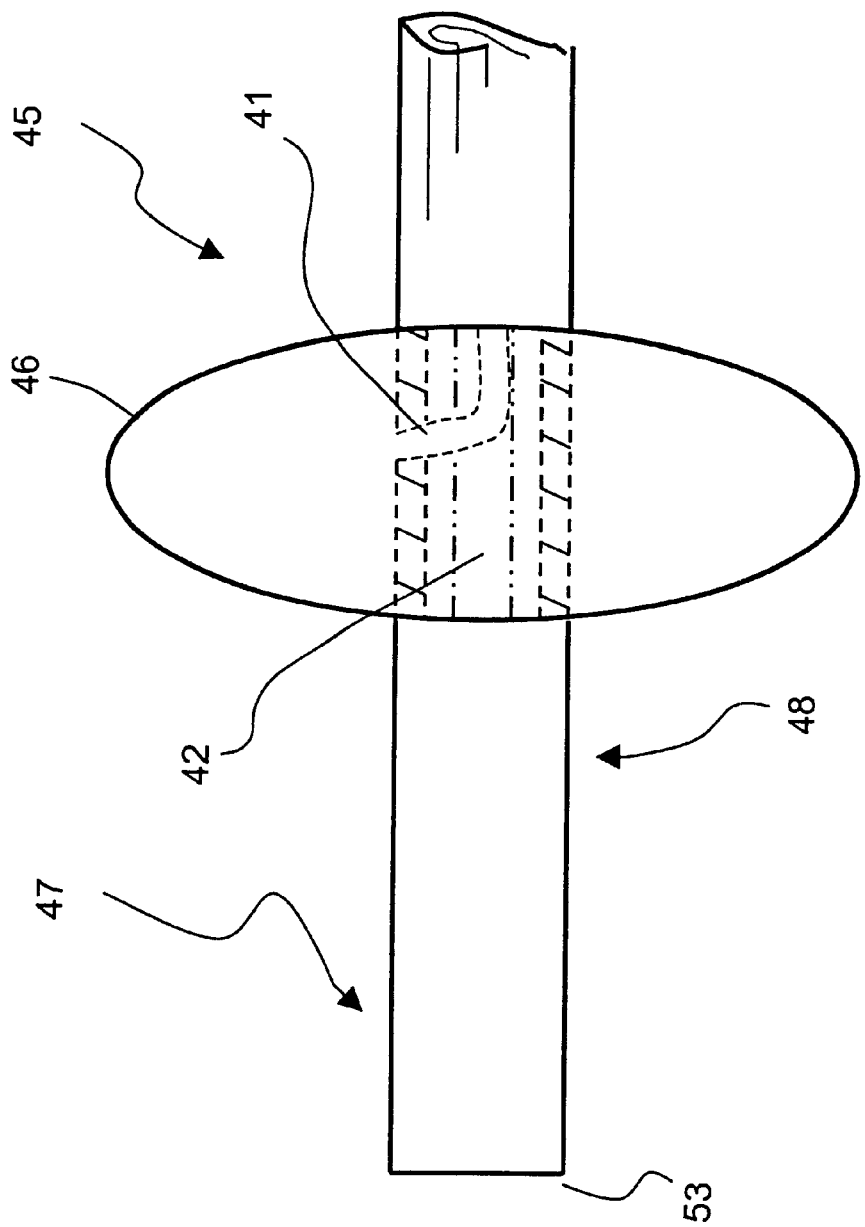
FIG. 11 is a first step of deploying a tissue-contactor member of the catheter system according to the second preferred embodiment in FIG. 10 for treating the tissue of an annular organ structure.
Figure 12:
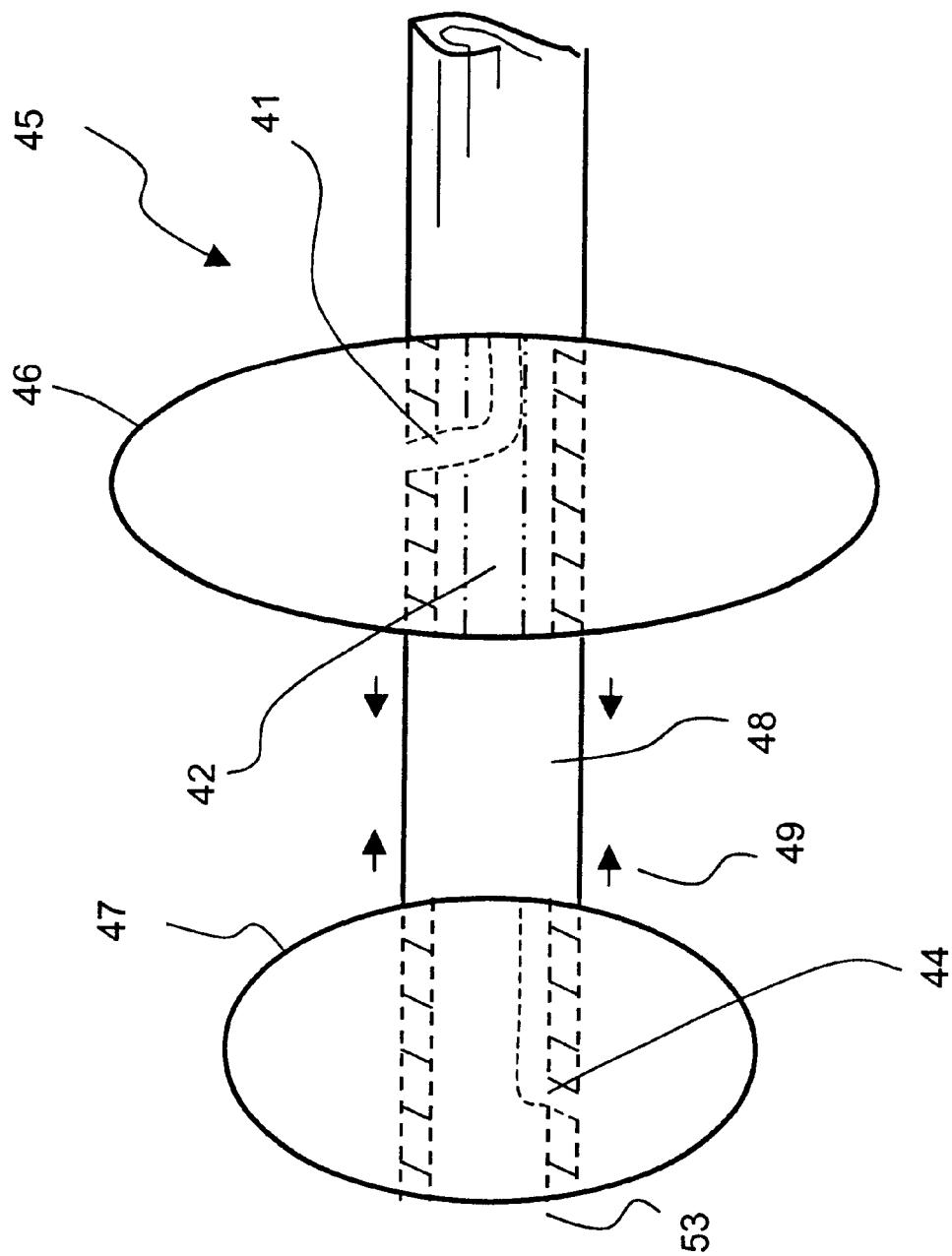
FIG. 12 is a second step of deploying a tissue-contactor member of the catheter system according to the second preferred embodiment in FIG. 10 for treating the tissue of an annular organ structure.
Figure 13:
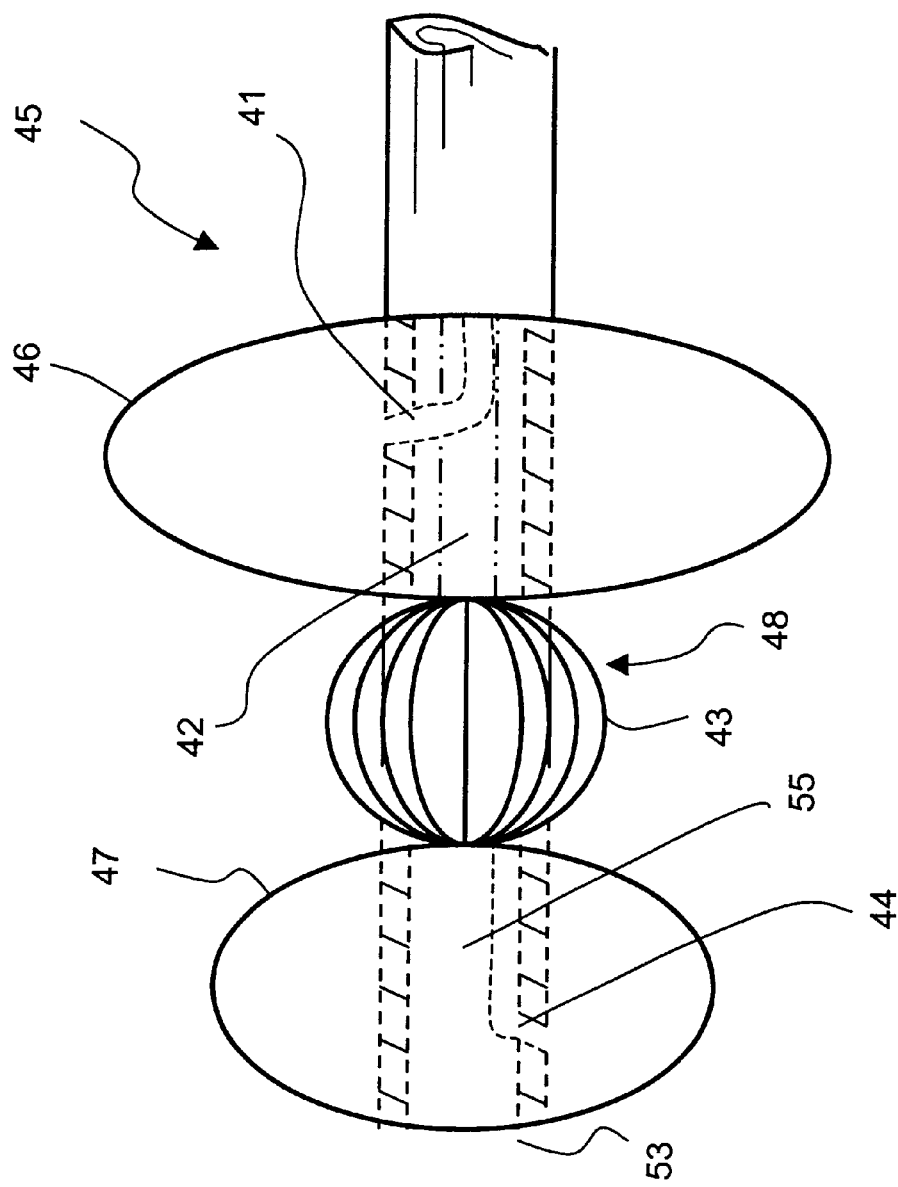
FIG. 13 is a third step of deploying a tissue-contactor member of the catheter system according to the second preferred embodiment in FIG. 10 for treating the tissue of an annular organ structure.

FIG. 10 shows a second preferred embodiment of a catheter system comprising a flexible tissue-contactor member 45 having electrode element means at its distal tip section 2 constructed in accordance with the principles of the present invention. The steps for deploying the tissue-contactor member 45 are shown in FIGS. 11 to 13. FIG. 11 shows a first step of deploying a tissue-contactor member 45 of the catheter system 1 according to the second preferred embodiment in FIG. 10 for treating the tissue of an annular organ structure. The flexible tissue-contactor member 45 comprises a proximal balloon 46 as the enlarged proximal region, the distal balloon 47 as the enlarged distal region, and a basket electrode element means 48 as the middle region. The outer diameter of the basket electrode element means 48 of the middle region is smaller than that of either enlarged end region 46, 47 so that the annulus is "compressively sandwiched" for tissue treatment.

The techniques to inflate and deflate a balloon 46 or 47 by infusing physiologic liquid through the liquid passageway 41 or 44 inside a lumen 55 are well known to one who is skilled in the art and do not form a part of the present invention. Other types of balloons, such as double-balloon, porous balloon, microporous balloon, channel balloon or the like that meet the principles of the present invention may be equally herein applicable.

After the first balloon 46 is inflated and sits appropriately at the upstream side of the annulus, a second balloon 47 is also inflated subsequently. At this moment of operations, the annulus of the annular organ structure is positioned loosely between the two end balloons 46 and 47. By relaxing or compressing axially the middle section therebetween (indicated by the arrows 49 in FIG. 12), the annulus is "compressively sandwiched" as defined in the present invention. A "sandwiched" annulus of the present invention generally exhibits certain degree of tightness or compressing.

FIG. 13 shows a third step of deploying a tissue-contactor member 45 of the catheter system according to the second preferred embodiment in FIG. 10 for treating the tissue of an annular organ structure, comprising deployment of the electrode element means 48. The electrode element means 48 may comprise a plurality of basket members that are expandable radially outwardly with a conductive surface 43 on each basket member facing outwardly. Other surface areas of the basket members away from the conductive surface 43 are insulated and not conductive. As disclosed and well known to a skilled artisan, an electrical conductor means 62 for transmitting high frequency current from a high frequency current generator 61 to the electrode elements 48 is provided.

In a preferred embodiment, a method for operating a catheter system of the present invention for repairing a valvular annulus, the method may comprise: (a) percutaneously introducing the catheter system through a blood vessel to a site of the valvular annulus or introducing the catheter system through a thoroscopy port into a heart or optionally injecting the heat shapeable biomaterial during an open heart surgery; (b) positioning the tissue-contactor member of the catheter shaft on the inner wall of the valvular annulus; (c) advancing the electrode elements for contacting the electrode elements with tissue of the valvular annulus; (d) optionally injecting heat shapeable biomaterial at the site of the valvular annulus defect; and (e) applying high frequency current through the electrical conductor means to the electrode elements for repairing the valvular annulus defect.

Figure 14:
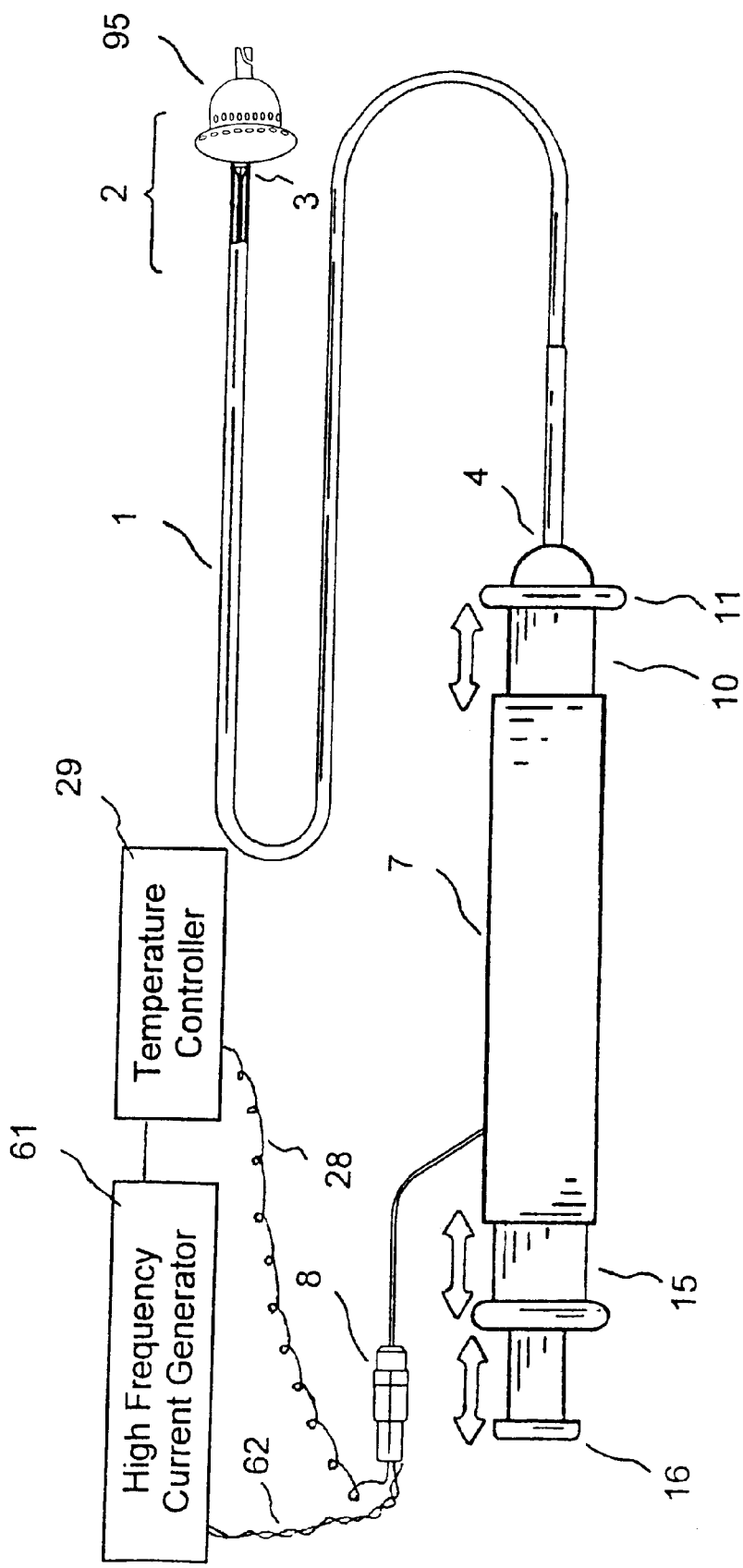
FIG. 14 is a third preferred embodiment of a catheter system having a deployed flexible tissue-contactor member and electrode element means at its distal tip section constructed in accordance with the principles of the present invention.

FIG. 14 shows a third preferred embodiment of a catheter system having a deployed flexible tissue-contactor member 95 and electrode element means at its distal tip section constructed in accordance with the principles of the present invention. The acorn-shaped tissue-contactor member 95 is to compressively sandwich a target annulus from two sides of the annulus at about 90 degrees to each other.

Figure 15:
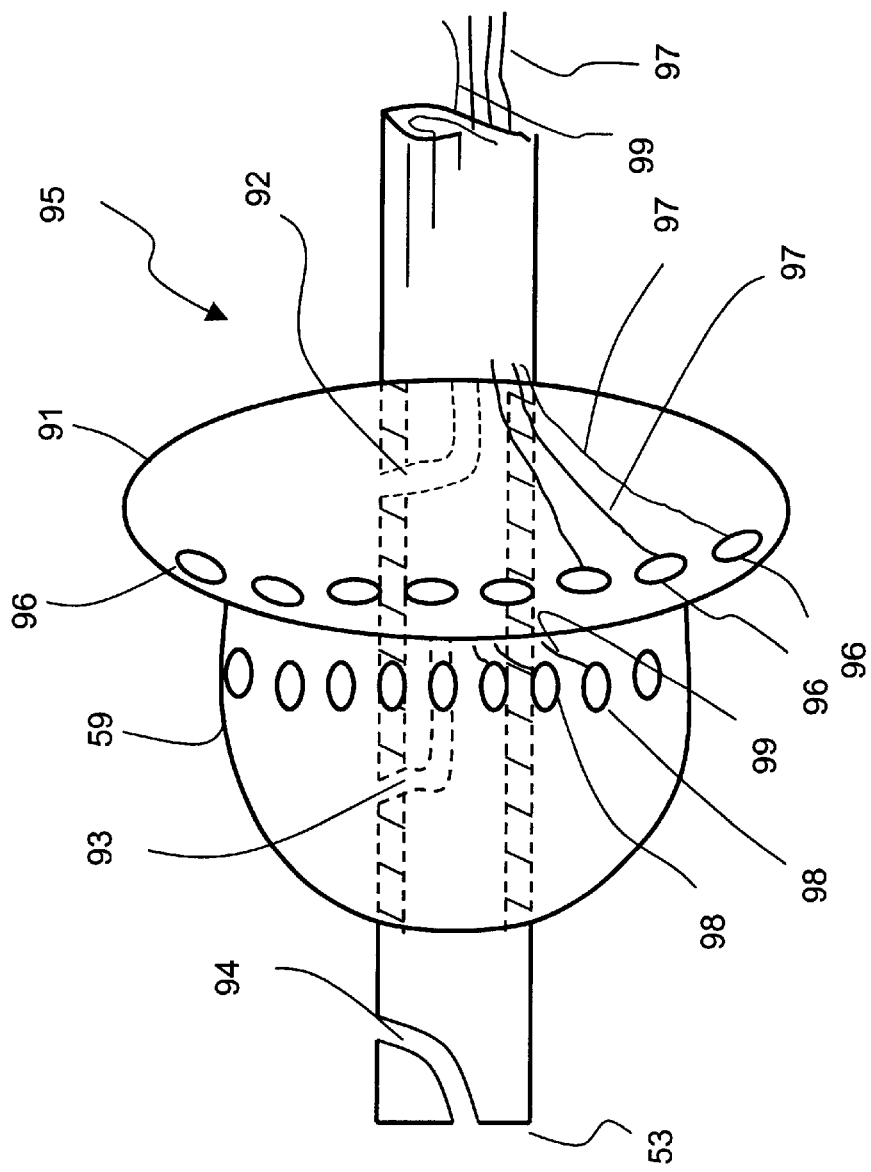
FIG. 15 is a detailed cross-sectional view of the distal tip section of the catheter system according to the third preferred embodiment in FIG. 14, comprising a deployed tissue-contactor member for treating the tissue of an annular organ structure.

FIG. 15 shows a detailed cross-sectional view of the distal tip section 2 of the catheter system 1 according to the third preferred embodiment in FIG. 14, comprising a deployed tissue-contactor member 95 for treating the tissue of an annular organ structure. In an example of mitral annulus treatment for illustration purposes, the first balloon 91 is intended to lay on top of the annulus while the flexible electrode elements 96 made of conductive elastomer material are intended to provide sufficient therapeutic energy for treating the annulus. The second balloon 59 is intended to lay against the inner wall of the annulus so that the flexible electrode elements 98 made of conductive elastomer material are intended to provide sufficient therapeutic energy for treating the leaflets. As is well known to one who is skilled in the art of balloon construction and the high frequency ablation technology, an electrical conductor means 97 or 99 for transmitting high frequency current to each electrode 96 or 98 is provided individually to the energy source while physiologic liquid to each balloon 91, 59 through a liquid passageway 92, 93 is also provided.

In an alternate embodiment, the flexible electrode elements 96, 98 may comprise a plurality of discrete elements, a plurality of contiguous elements, or a plurality of discrete element groups, each group comprising at least one electrode element. The arrangement of different styles of electrode elements is to facilitate treating a desired portion or a complete annular tissue under various modes. It is also well known to one skilled in the art that the flexible electrode means of the present invention may be constructed of an elongate flexible conductive electrode or with a conductive surface. In one example, an elongate flexible conductive electrode may comprise a metal-containing elastic (stretchable) electrode made of similar constructing material of the balloon. In a further embodiment, the elongate flexible conductive electrode may be a separate conductive elastic band (like a party rubber band) that is deployed between the exterior surface of the balloon and the inner wall of the annulus.

One advantage of the current embodiment in FIG. 15 is to provide physiologic liquid to inflate a balloon for repairing the valvular defect, whereas the liquid in the balloon serves as a heat sink to dissipate the heat generated from the high frequency electrode elements contacting the tissue. By continuously diverting the excess heat from the electrode-tissue contact site, the treatment efficiency can be substantially enhanced to cause quality desired shrinkage or tightening of the tissue of the annulus. The requirement for the high frequency power can therefore be significantly reduced. The energy required from the high frequency current generator is generally less than 100 watts in tissue ablation, preferably less than 10 watts because of the heat-dissipating embodiment of the present invention for repairing an annulus.

The catheter system of the present invention may also comprise a guidewire adaptive mechanism, such as a guidewire channel 94 located at about the balloon distal end 53 in FIG. 15 for the catheter to ride on a guidewire to the desired location for tissue treatment.

In one embodiment, a method for operating a catheter system for repairing an annulus comprises compressively sandwiching the annulus by a tissue-contactor member having electrode elements and delivering high frequency energy at or near the annulus through the electrode elements. Further, the method for repairing an annulus having valvular leaflets further comprises delivering high frequency energy to the leaflets.

In another preferred embodiment, a method for operating a catheter system for repairing an annulus may comprise compressively sandwiching the annulus by a tissue-contactor member and delivering high frequency energy to the annulus, wherein the tissue-contactor member is configured to have a narrow middle region between a radially enlarged distal region and a radially enlarged proximal region. In a further embodiment, the method for operating a catheter system for repairing an annulus comprises: (a) introducing the catheter system of the present invention through a bodily opening to an annulus; (b) deploying the tissue-contactor member of the catheter shaft at about the inner wall of the annulus; (c) positioning the electrode elements so as to enable the electrode elements contacting said inner wall of the annulus; and (d) applying high frequency current through the electrical conductor means to the electrode elements for repairing the annulus.

The tissue of the heart valve in the procedures may be selected from the group consisting of valvular annulus, chordae tendinae, valve leaflet, and papillary muscles. The high frequency current in the procedures may be selected from the group consisting of radiofrequency current, microwave current, ultrasound current, and combination thereof.

A temperature sensor 27, either a thermocouple type or a thermister type, is constructed at the proximity of the electrode 9B (shown in FIG. 6) to measure the tissue contact temperature when high frequency energy is delivered. A temperature sensing wire 28 from the thermocouple or thermister is connected to one of the contact pins of the connector 8 and externally connected to a transducer and to a temperature controller 29. The temperature reading is thereafter relayed to a closed-loop control mechanism to adjust the high frequency energy output. The high frequency energy delivered is thus controlled by the temperature sensor reading or by a pre-programmed control algorithm.

This invention also discloses a method for repairing a valvular annulus defect, the method comprising injecting a heat shapeable biomaterial formulated for in vivo administration by injection via a catheter system at a site of the valvular annulus defect; and applying heat sufficient to shape the biomaterial and immobilize the biomaterial at about the annulus defect.

The term "shapeable biomaterial" as used herein is intended to mean any biocompatible material that changes its shape, size, or configuration at an elevated temperature without significantly affecting its composition or structure. The shaping of a shapeable biomaterial is usually accomplished by applying moderate energy. For example, a crosslinked material is structurally different from a non-crosslinked counterpart and is not considered as a shaped material. The elevated temperature in this invention may range from about 39° C. to about 45° or higher, wherein the heat is below a temperature for effecting crosslinking of the biomaterial.

The biomaterial may comprise a matrix of collagen, a connective tissue protein comprising naturally secreted extracellular matrix, a heat shapeable polymer, or the like.

The term "matrix of collagen" as used herein is intended to mean any collagen that is injectable through a suitable applicator, such as a catheter, a cannula, a needle, a syringe, or a tubular apparatus. The matrix of collagen as a shapeable biomaterial of the present invention may comprise collagen in a form of liquid, colloid, semi-solid, suspended particulate, gel, paste, combination thereof, and the like. Devore in PCT WO 00/47130 discloses injectable collagen-based system defining matrix of collagen, entire disclosure of which is incorporated herein by reference.

The shapeable biomaterial may further comprise a pharmaceutically acceptable carrier for treating the annulus defect and a drug is loaded with the pharmaceutically acceptable carrier, wherein the drug is selected from a group consisting of an anti-clotting agent, an anti-inflammatory agent, an anti-virus agent, an antibiotics, a tissue growth factor, an anesthetic agent, a regulator of angiogenesis, a steroid, and combination thereof.

The connective tissue protein comprising naturally secreted extracellular matrix as a shapeable biomaterial of the present invention may be biodegradable and has the ability to promote connective tissue deposition, angiogenesis, and fibroplasia for repairing a tissue defect. U.S. Pat. No. 6,284,284 to Naughton discloses compositions for the repair of skin defects using natural human extracellular matrix by injection, entire contents of which are incorporated herein by reference. Bandman et al. in U.S. Pat. No. 6,303,765 discloses human extracellular matrix protein and polynucleotides which identify and encode the matrix protein, wherein the human extracellular matrix protein and its polynucleotides may form a shapeable biomaterial of the present invention.

The shapeable polymer as a biomaterial in the present invention may also comprise biodegradable polymer and non-biodegradable polymer, including prepolymer and polymer suspension. In one embodiment, the shapeable polymer in this invention may be selected from a group consisting of silicone, polyurethane, polyamide, polyester, polystyrene, polypropylene, polyacrylate, polyvinyl, polycarbonate, polytetrafluoroethylene, poly (1-lactic acid), poly (d, 1-lactide glycolide) copolymer, poly(orthoester), polycaprolactone, poly (hydroxybutyrate/hydroxyvaleerate) copolymer, nitrocellulose compound, polyglycolic acid, cellulose, gelatin, dextran, and combination thereof.

Slepian et al. in U.S. Pat. No. 5,947,977 discloses a novel process for paving or sealing the interior surface of a tissue lumen by entering the interior of the tissue lumen and applying a polymer to the interior surface of the tissue lumen. Slepian et al. further discloses that the polymer can be delivered to the lumen as a monomer or prepolymer solution, or as an at least partially preformed layer on an expansible member, the entire contents of which are incorporated herein by reference. The polymer as disclosed may be suitable as a component of the shapeable biomaterial of the present invention.

A method for joining or restructuring tissue consisting of providing a preformed sheet or film which fuses to tissue upon the application of energy is disclosed in U.S. Pat. No. 5,669,934, entire contents of which are incorporated herein by reference. Thus, the protein elements of the tissue and the collagen filler material can be melted or denatured, mixed or combined, fused and then cooled to form a weld joint. However, the heat shapeable biomaterial of the present invention may comprise collagen matrix configured and adapted for in vivo administration by injection via a catheter system at a site of the tissue defect; and applying heat sufficient to shape the biomaterial and immobilize the biomaterial at about the tissue defect, but not to weld the tissue.

An injectable bulking agent composed of microspheres of crosslinked dextran suspended in a carrier gel of stabilized hyaluronic acid is marketed by Q-Med AB (Uppsala, Sweden). In one embodiment of applications, this dextran product may be injected submucosally in the urinary bladder in close proximity to the ureteral orifice. The injection of dextran creates increased tissue bulk, thereby providing coaptation of the distal ureter during filling and contraction of the bladder. The dextran microspheres are gradually surrounded by body's own connective tissue, which provides the final bulking effect. The heat shapeable polymer of the present invention may comprise dextran configured and adapted for in vivo administration by injection via a catheter system at a site of the tissue defect; and applying heat sufficient to shape the biomaterial and immobilize the biomaterial at about the tissue defect.

Sinofsky et al. in U.S. Pat. No. 5,100,429 discloses an uncured or partially cured, collagen-based material delivered to a selected site in a blood vessel and is crosslinked to form an endoluminal stent, entire contents of which are incorporated herein by reference. The collagen-based material as disclosed may form a component of the shapeable biomaterial of the present invention. Edwards in PCT WO 01/52930 discloses a method and system for shrinking dilatations of a body, removing excess, weak or diseased tissues and strengthening remaining tissue of the lumen walls, the entire contents of which are incorporated herein by reference. However, Edwards does not disclose a method for repairing a tissue defect comprising: injecting a heat shapeable biomaterial formulated for in vivo administration by injection via a percutaneous delivery system at a site of the tissue defect; and applying heat to the biomaterial and a portion of the tissue defect adapted for shaping the biomaterial, the heat being below a temperature sufficient for effecting crosslinking of the biomaterial and the portion of the tissue defect.

Therefore, it is a further embodiment to provide a method for repairing a tissue defect comprising: injecting a heat shapeable biomaterial formulated for in vivo administration by injection via a percutaneous delivery system at a site of the tissue defect; and applying heat to the biomaterial and a portion of the tissue defect adapted for shaping the biomaterial, the heat being below a temperature sufficient for effecting crosslinking of the biomaterial and the portion of the tissue defect, the tissue defect may comprise vulnerable plaque, calcified tissue, or other lesions of atherosclerosis.

From the foregoing, it should now be appreciated that an improved catheter system and methods having electrode element means and high frequency current energy intended for tightening and stabilizing the tissue of an annular organ structure has been disclosed. It is generally applicable for repairing an annular organ structure of a heart valve, an annular organ structure of a venous valve, a valve leaflet, chordae tendinae, papillary muscles, and the like. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system for repairing an annular organ structure comprising:
    a flexible catheter shaft having a distal tip section, a distal end, a proximal end, and at least one lumen extending between the distal end and the proximal end;
    a flexible tissue-contactor member located at the distal tip section and inside the at least one lumen of said catheter shaft for contacting an inner wall of the annular organ structure, wherein said tissue-contactor member is deployable out of the at least one lumen by a tissue-contactor deployment mechanism and is expandable upon deployment configured to have a narrow middle region between an enlarged distal region and an enlarged proximal region suitable for compressively sandwiching said inner wall of the annular organ structure;
    a plurality of electrode elements located at a periphery of the middle region of said tissue-contractor member suitable for contacting said inner wall of the annular organ structure;
    a handle attached to the proximal end of the catheter shaft, wherein the handle comprises the tissue-contactor deployment mechanism; and
    a high frequency current generator, wherein an electrical conductor means for transmitting high frequency current to said electrode elements is provided.

2. The catheter system of claim 1, wherein the electrode elements are made of conductive elastomer material.

3. The cater system of claim 2, wherein the tissue-contactor member is a biocompatible balloon whose fabricating material is selected from the group consisting of silicone, latex, polyurethane, fluoro-elastomer, polypropylene, polyethylene, polyethylene terephthalate, nylon, and a combination thereof.

4. The catheter system of claim 3, wherein the tissue-contactor member comprises a distal end, a proximal end and a plurality of open channels therebetween for a fluid to pass from the proximal end of said tissue-contactor member to the distal end of said tissue-contactor member.

5. The catheter system of claim 1, wherein the annular organ structure is selected from the group consisting of a mitral valve, a tricuspid valve, a pulmonary valve, an aortic valve, and a venous valve.

6. The catheter system of claim 1, wherein the annular organ structure is a sphincter annulus.

7. The catheter system of claim 1 further comprising at least one temperature sensor mounted at one of the electrode elements adapted for measuring temperature of the inner wall of the annular organ structure.

8. The catheter system of claim 5 or 6, wherein said tissue-contactor member comprises an expandable construct with a plurality of expandable members enabling said tissue-contactor member to expand radially upon deployment, and wherein said tissue-contactor member further comprises a first expandable balloon located proximal of the expandable construct suitable for positioning said balloon at an upstream side of the valvular annulus and a second expandable balloon located distal of the expandable construct adapted for compressively sandwiching the inner wall of said annular organ structure between the expanded first balloon and the expanded second balloon.

9. A method for operating a catheter system for repairing an annulus comprising compressively sandwiching said annulus by a tissue-contactor member having electrode elements and delivering high frequency energy at or near said annulus through said electrode elements, wherein the catheter system comprises a flexible catheter shaft having a distal tip section, a distal end, a proximal end, and at least one lumen extending between the distal end and the proximal end; a flexible tissue-contactor member located at the distal tip section and inside the at least one lumen of said catheter shaft for contacting an inner wall of the annulus, wherein said tissue-contactor member is deployable out of the at least one lumen by a tissue-contactor deployment mechanism and is expandable upon deployment configured to have a narrow middle region between an enlarged distal region and an enlarged proximal region suitable for compressively sandwiching said inner wall of the annulus; a plurality of electrode elements located at the periphery of the tissue-contactor member suitable for contacting said inner wall of the annulus; a handle attached to the proximal end of the catheter shaft, wherein the handle comprises the tissue-contactor deployment mechanism; and a high frequency current generator, wherein an electrical conductor means for transmitting high frequency current to said electrode elements is provided;

the method comprising:

(a) introducing the catheter system through a bodily opening to an annulus;

(b) deploying the tissue-contactor member of the catheter shaft at about the inner wall of the annulus;

(c) postioning the electrode elements so as to enable the electrode elements compressively sandwiching said inner wall of the annulus; and (d) applying high frequency current through the electrical conductor means to the electrode elements for repairing the annulus.

10. The method for operating a catheter system for repairing an annulus of claim 9, wherein the tissue-contactor member is a biocompatible balloon whose fabricating material is selected from the group consisting of silicone, latex, polyurethane, fluoro-elastomer, polypropylene, polyethylene, polyethylene terephthalate, nylon, and a combination thereof.

11. The method for operating a catheter system for repairing an annulus of claim 9, wherein the electrode elements are made of conductive elastomer material.

12. The method for operating a catheter system for repairing an annulus of claim 9, wherein the annulus is selected from the group consisting of a mitral valve, a tricuspid valve, a pulmonary valve, an aortic valve, and a venous valve.

13. The method for operating a catheter system for repairing an annulus of claim 9, wherein the tissue-contactor member comprises a distal end, a proximal end and a plurality of open channels therebetween for a fluid to pass from the proximal end of said tissue-contactor member to the distal end of said tissue-contactor member.

14. The method for operating a catheter system for repairing an annulus of claim 9, wherein the high frequency current is delivered to said plurality of electrodes in a mode selected from the group consisting of individual mode, pulsed mode, programmed mode, and simultaneous mode.

15. The method for operating a catheter system for repairing an annulus of claim 9, wherein the high frequency current is selected from the group consisting of radiofrequency current, microwave current, ultrasound current, and combination thereof.

16. The method for operating a catheter system for repairing an annulus of claim 9, wherein the tissue-contactor member is a biocompatible balloon whose fabricating material is selected from the group consisting of silicone, latex, polyurethane, fluoro-elastomer, polypropylene, polyethylene, polyethylene terephthalate, nylon, and a combination thereof.

17. The method for operating a catheter system for repairing an annulus of claim 9, wherein said tissue-contactor member comprises a basket construct with a plurality of expandable members enabling said tissue-contactor member to expand radially upon deployment, and wherein said tissue-contactor member further comprises a first expandable balloon located proximal of the basket construct and a second expandable balloon located distal of the basket construct adapted for compressively sandwiching the inner wall of said annulus between the expanded first balloon and the expanded second balloon.

18. The method for operating a catheter system for repairing an annulus of claim 9, wherein the annulus is a sphincter annulus.

* * * * *